(12) United States Patent
Kettlewell et al.

(10) Patent No.: US 8,133,336 B2
(45) Date of Patent: Mar. 13, 2012

(54) TISSUE-ADHESIVE MATERIALS (75) Inventors: Graeme Kettlewell, Yorkshire (GB); David Mandley, Yorkshire (GB); David Fortune, Yorkshire (GB); Ian Thompson, Yorkshire (GB); Diane Morris, Yorkshire (GB)

(73) Assignee: Tissuemed Limited, Leeds (GB)

( * ) Notice: Subject to any disclaimer, the term of this patent is extended or adjusted under 35 U.S.C. 154(b) by 429 days.

(21) Appl. No.: 12/278,252

(22) PCT Filed: Feb. 2, 2007

(86) PCT No.: PCT/GB2007/050049
§ 371 (c)(1),
(2), (4) Date: Aug. 4, 2008

(87) PCT Pub. No.: WO2007/088402
PCT Pub. Date: Aug. 9, 2007

(65) Prior Publication Data
US 2009/0044895 A1   Feb. 19, 2009

Related U.S. Application Data (60) Provisional application No. 60/780,122, filed on Mar. 8, 2006.

(30) Foreign Application Priority Data

Feb. 3, 2006 (GB) .................................. 0602192.7
Mar. 20, 2006 (EP) .................................. 06270031

(51) Int. Cl.
*B29C 65/00* (2006.01)

(52) U.S. Cl. ........................... 156/60; 156/325; 424/443

(58) Field of Classification Search ................... 156/325, 156/60; 424/443
See application file for complete search history.

(56) References Cited

U.S. PATENT DOCUMENTS

| | | |
|---|---|---|
| 4,179,337 A | 12/1979 | Davis et al. |
| 4,453,939 A | 6/1984 | Zimmerman et al. |
| 4,456,711 A | 6/1984 | Pietsch et al. |
| 4,503,034 A | 3/1985 | Maupetit et al. |
| 4,744,364 A | 5/1988 | Kensey |
| 4,804,691 A | 2/1989 | English et al. |
| 4,837,379 A | 6/1989 | Weinberg |

(Continued)

FOREIGN PATENT DOCUMENTS

CA  2 363 916 A1   7/2000

(Continued)

OTHER PUBLICATIONS

Don et al., "Studies on the Degradation Behavior of Chitosan-g-Poly (Acrylic Acid) Copolyers," Tamkang Journal of Science and Engineering 5(4):235-40 (2002).

(Continued)

*Primary Examiner* — Khanh P Nguyen
*Assistant Examiner* — Vishal I Patel
(74) *Attorney, Agent, or Firm* — LeClairRyan, a Professional Corporation (57) ABSTRACT

A multi-lamellar tissue-adhesive sheet comprises a structural layer or laminate conjoined to a tissue-contacting layer. The structural layer or laminate comprises one or more synthetic polymers having film-forming properties, and the tissue-contacting layer of material contains tissue-reactive groups. The synthetic polymers having film-forming properties are preferably biodegradable polyesters, and the tissue-reactive groups are most preferably NHS-ester groups.

24 Claims, 2 Drawing Sheets

U.S. PATENT DOCUMENTS

| | | | |
|---|---|---|---|
| 4,911,926 A | 3/1990 | Henry et al. |
| 4,913,903 A | 4/1990 | Sudmann et al. |
| 4,940,737 A | 7/1990 | Braatz et al. |
| 5,017,229 A | 5/1991 | Burns et al. |
| 5,066,521 A | 11/1991 | Morsy |
| 5,066,709 A | 11/1991 | Chaudhuri et al. |
| 5,122,614 A | 6/1992 | Zalipsky |
| 5,135,751 A | 8/1992 | Henry et al. |
| 5,162,430 A | 11/1992 | Rhee et al. |
| 5,209,776 A | 5/1993 | Bass et al. |
| 5,292,362 A | 3/1994 | Bass et al. |
| 5,304,595 A | 4/1994 | Rhee et al. |
| 5,306,504 A | 4/1994 | Lorenz |
| 5,312,435 A | 5/1994 | Nash et al. |
| 5,324,775 A | 6/1994 | Rhee et al. |
| 5,328,955 A | 7/1994 | Rhee et al. |
| 5,334,640 A | 8/1994 | Desai et al. |
| 5,410,016 A | 4/1995 | Hubbell et al. |
| 5,462,990 A | 10/1995 | Hubbell et al. |
| 5,468,811 A | 11/1995 | Moro et al. |
| 5,514,379 A | 5/1996 | Weissleder et al. |
| 5,527,856 A | 6/1996 | Rhee et al. |
| 5,571,181 A | 11/1996 | Li |
| 5,575,815 A | 11/1996 | Slepian et al. |
| 5,580,923 A | 12/1996 | Yeung et al. |
| 5,583,114 A | 12/1996 | Barrows et al. |
| 5,614,587 A | 3/1997 | Rhee et al. |
| 5,643,464 A | 7/1997 | Rhee et al. |
| 5,752,974 A | 5/1998 | Rhee et al. |
| 5,770,229 A | 6/1998 | Tanihara et al. |
| 5,786,421 A | 7/1998 | Rhee et al. |
| 5,791,352 A | 8/1998 | Reich et al. |
| 5,863,662 A | 1/1999 | Hornby et al. |
| 5,874,500 A | 2/1999 | Rhee et al. |
| 5,931,165 A | 8/1999 | Reich et al. |
| 5,989,215 A | 11/1999 | Delmotte et al. |
| 6,007,544 A | 12/1999 | Kim |
| 6,051,648 A | 4/2000 | Rhee et al. |
| 6,063,061 A | 5/2000 | Wallace et al. |
| 6,066,325 A | 5/2000 | Wallace et al. |
| 6,075,107 A | 6/2000 | Kothrade et al. |
| 6,166,130 A | 12/2000 | Rhee et al. |
| 6,264,702 B1 | 7/2001 | Ory et al. |
| 6,312,725 B1 | 11/2001 | Wallace et al. |
| 6,323,278 B2 | 11/2001 | Rhee et al. |
| 6,329,115 B1 | 12/2001 | Yamashita |
| 6,379,373 B1 | 4/2002 | Sawhney et al. |
| 6,387,978 B2 | 5/2002 | Ronan et al. |
| 6,391,049 B1 | 5/2002 | McNally et al. |
| 6,458,889 B1 | 10/2002 | Trollsas et al. |
| 6,495,127 B1 | 12/2002 | Wallace et al. |
| 6,534,591 B2 | 3/2003 | Rhee et al. |
| 6,548,729 B1 | 4/2003 | Seelich et al. |
| 6,566,406 B1 | 5/2003 | Pathak et al. |
| 6,624,245 B2 | 9/2003 | Wallace et al. |
| 6,649,162 B1 | 11/2003 | Biering et al. |
| 6,664,331 B2 | 12/2003 | Harris et al. |
| 6,673,093 B1 | 1/2004 | Sawhney |
| 6,676,962 B1 | 1/2004 | Müller |
| 6,689,148 B2 | 2/2004 | Sawhney et al. |
| 6,703,047 B2 | 3/2004 | Sawhney et al. |
| 6,733,774 B2 | 5/2004 | Stimmeder |
| 6,800,671 B1 | 10/2004 | Montgomery et al. |
| 6,818,018 B1 | 11/2004 | Sawhney |
| 6,833,408 B2 | 12/2004 | Sehl et al. |
| 6,869,938 B1 | 3/2005 | Schwartz et al. |
| 6,875,796 B2 | 4/2005 | Stedronsky |
| 6,887,974 B2 | 5/2005 | Pathak |
| 6,894,140 B2 | 5/2005 | Roby |
| 6,916,909 B1 | 7/2005 | Nicolas et al. |
| 6,921,412 B1 | 7/2005 | Black et al. |
| 6,923,961 B2 | 8/2005 | Liu et al. |
| RE38,827 E | 10/2005 | Barrows et al. |
| 6,989,192 B2 | 1/2006 | Husemann et al. |
| 7,009,034 B2 | 3/2006 | Pathak et al. |
| 7,057,019 B2 | 6/2006 | Pathak |
| 7,597,882 B2 | 10/2009 | Pathak et al. |
| 2002/0013408 A1 | 1/2002 | Rhee et al. |
| 2002/0042473 A1 | 4/2002 | Trollsas et al. |
| 2002/0106409 A1 | 8/2002 | Sawhney et al. |
| 2002/0114775 A1 | 8/2002 | Pathak |
| 2002/0165337 A1 | 11/2002 | Wallace et al. |
| 2003/0119985 A1 | 6/2003 | Sehl et al. |
| 2003/0133967 A1 | 7/2003 | Ruszczak et al. |
| 2003/0149173 A1 | 8/2003 | Rhee et al. |
| 2004/0102797 A1 | 5/2004 | Golden et al. |
| 2004/0121951 A1 | 6/2004 | Rhee |
| 2004/0131554 A1 | 7/2004 | Rowe et al. |
| 2004/0138329 A1 | 7/2004 | Hubbell et al. |
| 2004/0191277 A1 | 9/2004 | Sawhney et al. |
| 2004/0234574 A9 | 11/2004 | Sawhney et al. |
| 2004/0235708 A1 | 11/2004 | Rhee et al. |
| 2004/0247691 A1 | 12/2004 | Marx et al. |
| 2005/0002893 A1 | 1/2005 | Goldmann |
| 2005/0003012 A1 | 1/2005 | Woller et al. |
| 2005/0004599 A1 | 1/2005 | McNally-Heintzelman et al. |
| 2005/0008632 A1 | 1/2005 | Stimmeder |
| 2005/0010239 A1 | 1/2005 | Chefitz |
| 2005/0015036 A1 | 1/2005 | Lutri et al. |
| 2005/0069589 A1 | 3/2005 | Lowinger et al. |
| 2005/0074495 A1 | 4/2005 | Schwartz et al. |
| 2005/0085605 A1 | 4/2005 | Nathan |
| 2005/0096388 A1 | 5/2005 | Hunter et al. |
| 2005/0107578 A1 | 5/2005 | Williams et al. |
| 2005/0125012 A1 | 6/2005 | Houser et al. |
| 2005/0129733 A1 | 6/2005 | Milbocker et al. |
| 2005/0154125 A1 | 7/2005 | Rhee |
| 2005/0208095 A1 | 9/2005 | Hunter et al. |
| 2005/0215748 A1 | 9/2005 | Milbocker et al. |
| 2005/0228433 A1 | 10/2005 | Bucay-Couto et al. |
| 2005/0281866 A1 | 12/2005 | Jarrett et al. |
| 2006/0147409 A1 | 7/2006 | Pathak et al. |
| 2007/0286891 A1* | 12/2007 | Kettlewell et al. ............ 424/443 |
| 2010/0233246 A1 | 9/2010 | Sehl et al. |

FOREIGN PATENT DOCUMENTS

| | | |
|---|---|---|
| DE | 35 02998 A1 | 7/1986 |
| DE | 259 351 A | 8/1988 |
| DE | 198 59 611 A1 | 6/2000 |
| EP | 0 099 758 A2 | 2/1984 |
| EP | 0 226 264 A1 | 6/1987 |
| EP | 0 732 109 A1 | 9/1996 |
| EP | 0 846 477 A1 | 6/1998 |
| EP | 0 930 074 A1 | 7/1999 |
| EP | 1 003 571 B1 | 5/2000 |
| EP | 1 216 717 A1 | 6/2002 |
| EP | 1 216 718 A1 | 6/2002 |
| WO | WO 92/02238 | 2/1992 |
| WO | WO 92/14513 | 9/1992 |
| WO | WO 94/21306 | 9/1994 |
| WO | WO 96/22054 | 7/1996 |
| WO | WO 96/22797 | 8/1996 |
| WO | WO 96/31237 | 10/1996 |
| WO | WO 97/17025 | 5/1997 |
| WO | WO 97/22371 | 6/1997 |
| WO | WO 97/29715 | 8/1997 |
| WO | 98/16165 A1 | 4/1998 |
| WO | 98/32474 A1 | 7/1998 |
| WO | WO 98/48716 | 11/1998 |
| WO | WO 99/15210 | 4/1999 |
| WO | WO 99/52481 | 10/1999 |
| WO | WO 00/02539 | 1/2000 |
| WO | 00/10618 A | 3/2000 |
| WO | WO 00/38752 | 7/2000 |
| WO | WO 00/59380 A3 | 10/2000 |
| WO | WO 01/30405 | 5/2001 |
| WO | WO 01/30410 | 5/2001 |
| WO | WO 01/56475 | 8/2001 |
| WO | WO 01/58452 | 8/2001 |
| WO | WO 02/09792 A1 | 2/2002 |
| WO | WO 02/34304 | 5/2002 |
| WO | WO 02/058749 A2 | 8/2002 |
| WO | WO 03/020824 A1 | 3/2003 |
| WO | 03/094898 A2 | 11/2003 |
| WO | 2004060405 A2 | 7/2004 |
| WO | 2004/087227 A1 | 10/2004 |
| WO | WO 2004/087227 * | 10/2004 |

| WO | WO 2004087227 A1 * | 10/2004 |
| WO | 2004108179 A1 | 12/2004 |
| WO | 2005055958 A2 | 6/2005 |
| WO | 2005089659 A1 | 9/2005 |
| WO | 2007127198 A2 | 11/2007 |

OTHER PUBLICATIONS

Israelachvili, "The Different Faces of Poly(ethylene glycol)," Proc. Natl. Acad. Sci. USA 94:8378-9 (1997).

Birch et al., "Methylene Blue Based Protein Solder for Vascular Anastomoses: An In Vitro Burst Pressure Study," *Lasers in Surgery and Medicine* 26:323-329 (2000).

Delgado et al., "The Uses and Properties of PEG-Linked Proteins," *Critical Reviews in Therapeutic Drug Carrier Systems* 9(3,4):249-304 (1992).

Duval et al., "Synthesis and Characterization of Some Covalent Dextran-Polyoxyethyleneglycol Derivatives," *Carbohydrate Polymers* 15:233-242 (1991).

Erout et al., "Radical-Initiated Copolymers of N-vinyl Pyrrolidone and N-Acryloxy Succinimide: Kinetic and Microstructure Studies," *Polymer* 37(7):1157-1165 (1996).

Harris et al., "Synthesis and Characterization of Poly(ethylene Glycol) Derivatives," *J. Polymer Sci.* 22:341-352 (1984).

Mandley et al., "Photon Activated Biological Adhesives in Surgery," *International Journal of Adhesion & Adhesives* 20:97-102 (2000).

Nishi & Kotaka, "Complex-Forming Poly(oxyethylene):Poly(acrylic acid) Interpenetrating Polymer Networks. 1. Preparation, Structure, and Viscoelastic Properties," *Macromolecules* 18(8):1519-1525 (1985).

Sánchez-Chaves et al., "Poly (Vinyl Alcohol) Functionalized by Monosuccinate Groups. Coupling of Bioactive Amino Compounds," *Polymer* 39(13):2751-2757 (1998).

Zalipsky et al., "Attachment of Drugs to Polyethylene Glycols," *Eur. Polym. J.* 19(12):1177-1183 (1983).

Zalipsky et al., "Evaluation of a New Reagent for Covalent Attachment of Polyethylene Glycol to Proteins," *Biotechnology and Applied Biochemistry* 15:100-114 (1992).

Zalipsky et al., "Succinimidyl Carbonates of Polyethylene Glycol: Useful Reactive Polymers for Preparation of Protein Conjugates," *Polymer Reprints*, pp. 173-174 (1990).

Iwata et al., "A Novel Surgical Glue Composed of Gelatin and N-hydroxysuccinimide Activated Poly(L-glutamic acid): Part 1. Synthesis of Activated poly(L-glutamic acid) and its Gelation with Gelatin," *Biomaterials* 19:1869-1876 (1998).

Disley et al., "Covalent Coupling of Immunoglobulin G to a Poly(Vinyl)Alcohol-Poly(Acrylic Acid) Graft Polymer as a Method of Fabricating the Interfacial-Recognition Layer of a Surface Plasmon Resonance Immunosensor," Biosensors and Bioelectronics 13(3-4):383-396 (1998) (abstract only).

\* cited by examiner

Synthesis of poly(N-vinyl pyrrolidone$_{50}$-co-acrylic acid$_{25}$-co-acrylic acid-N-hydroxysuccinimide ester$_{25}$)

1. AIBN (0.1 mol %), DMSO, 80 °C, 18 hr
2. NHS (50 mol %), DCC (25 mol %), DMSO, 20 °C, 96 hr

TISSUE-ADHESIVE MATERIALS

This application is a U.S. national stage entry under 35 U.S.C. §371 of International Patent Application No. PCT/GB2007/050049, filed Feb. 2, 2007, which claims priority from U.S. Provisional Patent Application Ser. No. 60/780,122, filed Mar. 8, 2006; European Patent Application No. 06270031.5, filed Mar. 20, 2006; and Great Britain Patent Application No. 0602192.7, filed Feb. 3, 2006.

FIELD OF THE INVENTION

This invention relates to a flexible sheet suitable for use as a tissue adhesive and sealant, and intended for topical application to internal and external surfaces of the body, for therapeutic purposes. The invention also relates to a process for the preparation of such a sheet, and to methods of using such a sheet. In particular the invention relates to a self-adhesive, biocompatible and hydratable polymeric sheet, which may be used for therapeutic purposes such as wound healing, joining, sealing and reinforcing weakened tissue, and for delivery of therapeutic agents, and to a process for preparing, and methods of using, such a sheet. The invention further relates to implantable medical devices coated with similar material to that of the sheet.

BACKGROUND OF THE INVENTION

There is considerable interest in the use, for a number of surgical or other therapeutic applications, of materials that adhere to biological tissues, eg as an alternative to the use of mechanical fasteners such as sutures, staples etc. Formulations of such materials that have hitherto been proposed include viscous solutions or gels that are either manufactured in that form or are prepared immediately prior to use by mixing of the ingredients. Such formulations are then applied to the tissue surface using a suitable applicator device such as a syringe.

Formulations of the type described above suffer from a number of disadvantages. If the formulation is of low viscosity, it may spread from the area of application and hence be difficult to apply precisely to the desired area of tissue. If the formulation is more viscous, on the other hand, it may be difficult to dispense. In either case, the formulation, being prepared in hydrated form, may have a limited lifetime and may be subject to premature curing. It may therefore be necessary for the whole of the formulation to be used at once or discarded. Also, the preparation of formulations immediately prior to use by mixing of ingredients is obviously laborious and time-consuming, and may require the use of additional apparatus. In addition to these drawbacks, the degree of adhesion between tissue surfaces that is provided by such formulations may be less than would be desired.

Formulations of tissue adhesive materials have also been applied to suitable supports for application to the tissue surface. The use of therapeutic materials in the form of a sheet, patch or film, for topical administration to either internal or external organs of the body, is well documented for a wide range of medical applications. A disadvantage of products proposed hitherto, however, is that the degree of adhesion to the underlying tissue in addition to their cohesive strength, particularly in the longer term, may be inadequate. While the initial adhesion may be satisfactory, the sheet may subsequently become detached from the tissue, often after only a few seconds or minutes, eg as a result of hydration of the sheet following its application. In addition, the flexibility of the product may be insufficient for it to conform readily to the surface to which it is applied, which may also have an adverse effect on its adhesion.

As a result of the inadequate adhesion of these products, it may be necessary to provide further reinforcement, eg through mechanical attachment using sutures, staples or the like. Alternatively, energy (eg light or heat energy) may be applied in order to initiate chemical bonding of the adhesive formulation to the underlying tissue, and hence bonding of the tissue surfaces to each other. Clearly, such approaches introduce further drawbacks. The use of mechanical fastenings such as sutures or staples is often the very thing that the use of such products is intended to replace or avoid. In many instances, the use of such fastenings is either not wholly effective (eg on the lung) or undesirable, as their introduction gives rise to further areas of tissue weakness. The use of external energy requires the provision and operation of a source of such energy. Such energy sources may be expensive and difficult to operate, particularly in the confines of an operating theatre or similar environment. Also, the use of external energy for attachment can be both time-consuming and (in some cases) requires significant careful judgement on the part of the surgeon, to evaluate when sufficient energy has been delivered to effect attachment without damaging the underlying tissue.

A disadvantage of sheet-type products for applications as described above is that they may lack the degree of flexibility that may be necessary or desirable for many applications. This is particularly so for products used in the increasingly important field of endoscopic (keyhole) surgery, which may require the product to be folded or rolled into a compact configuration prior to introduction into the body. Attempts to render such products more flexible, eg by the inclusion of plasticisers, may have the effect of reducing the adhesiveness of the product.

There have now been devised improvements to tissue-adhesive sheets or the like of the general type described above, and to related applications of tissue-adhesive material, that overcome or substantially mitigate the above-mentioned and/or other disadvantages of the prior art.

BRIEF SUMMARY OF THE INVENTION

According to a first aspect of the invention, there is provided a multi-lamellar tissue-adhesive sheet comprising a structural layer or laminate, which structural layer or laminate comprises one or more synthetic polymers having film-forming properties, and to which structural layer or laminate is conjoined a tissue-contacting layer of material containing tissue-reactive groups.

The sheet according to the invention is advantageous primarily in that it bonds effectively to tissue, enabling it to be used in a variety of medical applications. The sheet has been found to offer improved flexibility and yet to retain good adhesiveness. In preferred embodiments, the sheet exhibits good initial adhesion to the tissue to which it is applied (and may thus be described as "self-adhesive"), and furthermore remains well-adhered to the tissue over a longer timescale. Without wishing to be bound by any theory, it is believed that the initial adhesion of the sheet to the tissue is attributable to electronic bonding of the sheet to the tissue, and this is supplemented or replaced by covalent chemical bonding between the tissue-reactive functional groups of the formulation and the tissue, in particular between amine and/or thiol groups on the tissue surface and the tissue-reactive functional groups of the sheet.

Initial adhesion of the sheet to the tissue surface is believed to be due to Van der Waals forces and/or hydrogen bonding between the sheet and the tissue surface. On contact with the tissue surface the sheet becomes hydrated, thereby causing reaction between the tissue-reactive functional groups and the underlying tissue surface. Such reactions between the tissue-reactive functional groups and the underlying tissue result in high adhesion between the sheet and the tissue surface. The sheet may absorb physiological fluids (as a consequence of application onto exuding tissue surfaces), and any additional solutions used to hydrate the sheet following application (such fluids can be commonly used solutions used in surgical irrigation), becoming more compliant and adherent to the tissue surfaces, and thereby providing an adhesive sealant with haemostatic and pneumostatic functions.

The use of the sheet reduces or eliminates the need for additional means of mechanical attachment to the tissue (eg sutures or staples), or the need to provide external energy in the form of heat or light to bring about adherence of the sheet to the underlying tissue. Another advantage of the sheet according to the invention is that it is applied to the tissue as a preformed article, rather than being prepared by mixing of materials immediately prior to use.

In addition, because the sheet is, until hydrated upon and following contact with the tissue surface, essentially inactive, the sheet is not prone to premature reaction and as a result its shelf-life may be considerable, eg more than six months when stored appropriately at room temperature.

By the term "sheet" is meant an article with a thickness that is considerably less than its other dimensions. Such an article may alternatively be described as a patch or a film.

In preferred embodiments of the invention, the structural layer or laminate is a laminate comprising two or more discrete layers that are conjoined together. In particularly preferred embodiments, the laminate comprises alternating layers of polymer having film-forming properties and material containing reactive functional groups. In general, sheets comprising a structural laminate have been found to perform better, in terms of adhesion to tissue and/or elasticity and/or maintenance of structural integrity, than sheets with a single structural layer.

In such a case, the sheet according to the invention most preferably comprises an even number of layers, and in particular alternating layers of film-forming polymer and material containing reactive groups. The sheet may then be considered to comprises a structural laminate comprising n layers of film-forming polymer with n−1 layers of reactive material interspersed therebetween, and a tissue-contacting layer of tissue-reactive material. The value of n may be 1, in which case the sheet comprises simply a single structural layer and the tissue-contacting layer. Alternatively, n may be 2 or 3, in which case the sheet comprises 4 or 6 layers in total. Sheets in which n=2 are currently most preferred.

The material containing reactive functional groups may be the same as, or similar to, the tissue-reactive material of the tissue-contacting layer.

In another aspect of the invention, there is provided a device suitable for implantation in the human or animal body, which device carries on at least part of the external surface thereof a coating comprising one or more polymers with film-forming properties, at least part of said coating being conjoined to a layer of material comprising tissue-reactive functional groups.

In this aspect of the invention, the coating of film-forming polymer provides a means for attachment to the device of the material comprising tissue-reactive functional groups, the latter material providing a means for anchoring the device in its desired position within the body. This aspect of the invention may therefore be of particular utility in relation to implantable devices that would otherwise be difficult to fix in position within the body, for instance because they are made of a material that is chemically inert and not amenable to reaction with the surrounding tissue or with chemical linking groups.

In the following detailed description of the invention, reference is made primarily to embodiments of the invention that have the form of sheets. It will be appreciated, however, that analogous comments apply, where appropriate, to embodiments of the invention involving coatings on implantable devices.

In another aspect, the invention also provides a method of joining a tissue surface to another tissue, or of sealing a tissue surface, which method comprises applying to the tissue surface a sheet according to the first aspect of the invention.

The sheet according to the invention may also be used for the delivery of one or more therapeutically active or anti-infective agents to the site to which the sheet is applied. In such a case, the agent(s) may be incorporated into the sheet, eg by admixture with the other ingredients that are used in the manufacture of the sheet. Alternatively, the agent(s) may be covalently bound to a component of the sheet. However, in other embodiments, the sheet is free of therapeutically active agents. In a similar manner, one or more therapeutically active agents may be incorporated into the material applied to the external surface of an implantable device according to the second aspect of the invention.

DETAILED DESCRIPTION OF THE INVENTION

Abbreviations

| | |
|---|---|
| AAc | acrylic acid |
| AIBN | azo-iso-butyronitrile |
| DCC | dicyclohexylcarbodiimide |
| DCM | dichloromethane |
| DCU | dicyclohexylurea |
| DMF | dimethylformamide |
| DMSO | dimethyl sulfoxide |
| DPBS | Dulbecco's Phosphate-Buffered Saline |
| ENT | ear, nose and throat |
| HPC | hydroxypropylcellulose |
| IPA | iso-propanol |
| $M_n$ | number average molecular weight |
| $M_w$ | weight average molecular weight |
| MeOH | methanol |
| NHS | N-hydroxysuccinimide |
| NVP | N-vinyl pyrrolidone |
| PEG | polyethylene glycol |
| PLG | poly(DL-lactide-co-glycolide) |
| poly(VP-AAc) | copolymer of vinyl pyrrolidone and acrylic acid |
| poly(VP-AAc(NHS)) | copolymer of vinyl pyrrolidone and acrylic acid NHS ester |
| poly(VP-AAc-AAc(NHS)) | terpolymer of vinyl pyrrolidone, acrylic acid and acrylic acid NHS ester |

Nature of the Structural Layer or Laminate

The sheet according to the first aspect of the invention includes a structural layer or laminate that comprises at least one film-forming polymer. The structural layer or laminate may consist entirely or substantially entirely of film-forming polymer. In other embodiments, the structural layer or laminate consists largely of film-forming polymer. For instance, the structural layer or laminate may comprise more than 80%, more than 90% or more than 95% w/w of film-forming polymer.

A variety of suitable film-forming polymers may be used to form the first layer, provided that they exhibit suitable film-forming properties together with suitability for medical applications, in particular absence of toxicity, biocompatibility and, usually, biodegradability.

Most commonly, the first layer comprises just one film-forming polymer. Alternatively, the first layer may be formed from more than one film-forming polymer.

The film-forming polymer may be synthetic, or it may be, or may be derived from, a naturally-occurring material.

A particularly preferred group of synthetic polymers that may be suitable for use in the invention are biodegradable polyesters. Specific examples of such polymers are polylactic acid and polyglycolic acid, and copolymers and blends thereof. Other examples include polycaprolactones and polyhydroxyalkanoates, such as polyhydroxybutyrate, polyhydroxyvalerate and polyhydroxyhexanoate.

The currently most preferred polyester polymers for use in the invention are poly(lactide-co-glycolide) [also referred to as poly(lactic-co-glycolic acid)] copolymers, which are generally biodegradable and biocompatible, and are soluble in a wide range of organic solvents.

In the currently most preferred embodiments of the sheet, comprising a structural laminate, particularly preferred embodiments are those that comprise alternating layers of biodegradable polyester material and material containing reactive functional groups. Thus, in a specific aspect of the invention, there is provided a multi-lamellar tissue-adhesive sheet comprising a structural laminate, which laminate comprises n layers of a biodegradable polyester with n–1 layers of material containing reactive functional groups interspersed therebetween, and a tissue-contacting layer of tissue-reactive material, wherein n has a value of 1, 2 or 3, most preferably 2.

In such embodiments, the layer distal to the tissue-contacting layer is of polyester, which is substantially non-adhesive to tissue. Such sheets will therefore generally adhere only to the target tissue (to which the tissue-contacting layer, containing tissue-reactive functional groups, is applied), and not to surrounding tissues (eg the pleural or peritoneal wall).

Other examples of synthetic polymers that may be suitable are aminated polymers such as aminated PEGs (including those sold under the trade name JEFFAMINE) and polyallylamines.

Further film-forming polymers that may be suitable for use in the invention are polysaccharides, and in particular basic polysaccharides.

Nature of the Tissue-Contacting Layer

The sheet according to the first aspect of the invention has a tissue-contacting layer that comprises a material containing tissue-reactive functional groups. That material preferably comprises one or more polymers containing tissue-reactive functional groups.

By "tissue-reactive functional groups" is meant functional groups capable of reacting with other functional groups present in the tissue surface so as to form covalent bonds with the tissue. Tissues generally consist partly of proteins, which commonly contain thiol and primary amine moieties. Many functional groups such as imido ester, p-nitrophenyl carbonate, NHS ester, epoxide, isocyanate, acrylate, vinyl sulfone, orthopyridyl-disulfide, maleimide, aldehyde, iodoacetamide, and others, may react with thiols or primary amines, and therefore constitute "tissue-reactive functional groups". As used herein, the term NHS or NHS ester is intended to encompass not only N-hydroxysuccinimide itself, but also derivatives thereof in which the succinimidyl ring is substituted. An example of such a derivative is N-hydroxysulfosuccinimidyl and salts thereof, particularly the sodium salt, which may increase the solubility of the tissue-reactive material.

Tissue-reactive functional groups that may be of utility in the present invention are any functional groups capable of reaction (under the conditions prevalent when the formulation is applied to tissue, ie in an aqueous environment and without the application of significant amounts of heat or other external energy) with functional groups present at the surface of the tissue. The latter class of functional group includes thiol and amine groups, and tissue-reactive functional groups therefore include groups reactive to thiol and/or amine groups. Examples are:

- imido ester;
- p-nitrophenyl carbonate;
- NHS ester;
- epoxide;
- isocyanate;
- acrylate;
- vinyl sulfone;
- orthopyridyl-disulfide;
- maleimide;
- aldehyde; and
- iodoacetamide.

NHS ester is a particularly preferred tissue-reactive functional group.

In addition to tissue-reactive functional groups, the polymer(s) that make up the material of the second layer may contain functional groups that, whilst not themselves being reactive to the tissue to which the sheet is applied, do provide good contact adhesion between the sheet and the tissue. Such functional groups are referred to herein as "non-reactive functional groups". Examples of non-reactive functional groups include hydroxyl, heterocyclic amines or amides (eg in vinyl pyrrolidone residues) and, particularly, carboxyl groups (eg in acrylic acid residues).

It is particularly preferred that the tissue-reactive functional groups are activated derivatives of non-reactive functional groups. In certain embodiments, all of the non-reactive functional groups may be activated to form tissue-reactive functional groups. In other embodiments, only some of the non-reactive functional groups may be activated to form tissue-reactive functional groups. In the latter case, the strength of initial contact adhesion of the sheet to the tissue to which it is applied, and the strength of the longer term adhesion brought about by covalent reaction of the tissue-reactive functional groups with functional groups in the tissue may be varied and controlled by varying the proportion of the non-reactive groups that are in activated form.

NHS ester is a particularly preferred tissue-reactive functional group, and therefore preferred tissue-reactive polymers are NHS ester-rich polymers. Particularly preferred tissue-reactive polymers are poly(VP-AAc(NHS)) and poly(VP-AAc-AAc(NHS)) terpolymer.

Sufficiency of the degree of initial adhesion of a sheet to the tissue, by the bioadhesive polymer(s), can be quantitatively determined in vitro, for example by performing an adhesion strength test. This test is performed by allowing the sheet to adhere to a suitable substrate (secured in a fixed position), while the sheet itself is physically attached at a separate point to the load of a tensile testing apparatus, positioned so that, prior to the test, the sheet is not under load. The load cell is moveable along an axis substantially perpendicular to that along which the substrate is positioned. The test involves movement of the load cell away from the substrate, at a constant predetermined rate, until the sheet detaches from the substrate. The output of the test is a quantitative measure of the energy of adhesion for that sheet—ie the cumulative amount of energy required to break the interaction between the sheet and the substrate to which it is adhered. A suitable cumulative energy of adhesion for the sheet according to the invention would be not less than 0.5 mJ.

In certain embodiments of the invention, a preferred tissue-reactive polymer is poly(VP-AAc-AAc(NHS)) terpolymer. The carboxyl groups on poly(VP-AAc) may be converted to NHS esters by reaction with NHS in the presence of DCC (see Example 9). If the acid content of the poly(VP-AAc) is determined (in moles), the proportion of acid groups converted to tissue-reactive groups may be controlled by adding the desired mole percent of NHS.

Another tissue-reactive polymer that may be used, containing hydroxyl groups, is an activated form of HPC succinate, eg HPC succinate-NHS. In this case, some of the hydroxyl groups are activated with NHS via succinic acid linkage (see Example 11).

The properties of the tissue-adhesive sheet may be optimised by inclusion of other polymers and additives.

Property Enhancing Additives

Although in general the sheet according to the first aspect of the invention has adequate flexibility, it may nonetheless be desirable to further improve the flexibility, elasticity and/or wet-strength of the sheet by the addition of one or more plasticizers and elastomers to the structural layer or laminate and/or the tissue-contacting layer. In particular, low molecular weight species such as glycerol and low molecular weight PEG may be incorporated into the formulations to increase flexibility. Examples of suitable elastomers that may be incorporated into the product include poly(caprolactones), poly(urethanes) and poly(silicones). Such materials may increase the flexibility and/or elasticity of the sheet when added at levels of up to 30% by weight of the ingredients that make up the sheet. However, the inclusion of high levels of such materials may have a detrimental effect on the adhesive performance of the sheet. To offset this disadvantage, additives may be functionalised to include tissue-reactive functional groups that may participate in tissue-adhesion.

Buffers

The reaction between tissue-reactive functional groups on the sheet and functional groups on the surface of the tissue may vary with pH. It may therefore be preferable to buffer the tissue surface immediately prior to application or, more preferably, to include a buffer in the formulation used to prepare the sheet, in particular the tissue-contacting layer of the sheet. The mean work of adhesion of certain sheets according to the invention to explanted porcine liver may be improved by buffering the tissue surface with pH 10.5 phosphate/carbonate buffer.

Conjoining of Components of the Sheet During Manufacture

The materials of the structural layer or laminate and/or the tissue-contacting layer may be conjoined during the process of manufacture. Such conjoining may increase the physical strength of the sheet and may optimise the properties of the sheet, in particular in terms of the time required for biodegradation of the sheet after it has been applied.

Conjoining may be brought about by various means, including casting of component layers from common solvents. A further method involves a formulation from which the structural layer or laminate and/or tissue-contacting layer is prepared that comprises at least two functional groups which are capable of reacting with functional groups present in the material that is to be conjoined. This component will therefore act as a cross-linking agent. Preferably, the cross-linking agent contains at least two functional groups of the same form. Thus, the cross-linking agent is most preferably a homobifunctional or homopolyfunctional cross-linking agent.

Physical Form of the Sheet

The sheet may typically have an overall thickness of from 0.01 to 1 mm, typically 0.01 to 0.5 mm, and more commonly 0.015 to 0.2 mm or 0.015 to 0.1 mm, eg 0.015 to 0.05 mm.

In currently preferred embodiments, the thickness of the tissue-contacting layer is greater than the thickness of the structural layer or laminate. For instance, the tissue-contacting layer may have a thickness that accounts for more than 50% of the overall thickness of the sheet, or more than 60%.

The sheet may be produced with, or subsequently cut to, dimensions of from a few square millimeters up to several tens of square centimeters.

Manufacture of the Sheet

Most conveniently, the sheet according to the invention may be prepared by stepwise formation of the individual layers that make up the sheet.

The structural layer or (as is preferred) the layer of the structural laminate that is distal to the tissue-contacting layer may be prepared first, eg by casting a solution of the material that makes up that layer in a suitable solvent, either on a suitable plate or mould or onto a suitable release paper, eg a silicone-coated release paper. The cast solution is then dried or allowed to dry, optionally under conditions of elevated temperature and/or reduced pressure.

Successive layers of the structural laminate may then be cast onto the pre-formed first layer, followed in each case by drying to remove solvent, and where appropriate curing to achieve a desired degree of cross-linking. Curing is most preferably promoted by application of elevated temperatures (typically up to one hour or more at temperatures of up to 60° C. or higher).

Finally, the tissue-contacting layer may be cast onto the structural layer or laminate. Once again, this is preferably is followed by drying to remove solvent, and curing to achieve a desired degree of cross-linking. Curing preferably occurs at least partially at elevated temperatures (typically in excess of ten minutes and up to one hour or more at temperatures of up to 60° C.).

Each layer of the sheet may be cast in a single operation. Alternatively, particularly for layers that are relatively thick (ie that are thick relative to other layers of the sheet), a layer may be built up by successive casting of thinner sub-layers.

Once manufactured, and prior to use, the sheet according to the invention will typically have a water content of less than 10% w/w, and more commonly less than 5% w/w.

During manufacture an image or alphanumeric marking may be printed onto the surface of the individual layers of the sheet. This marking may be used to distinguish the tissue adhesive surface from the non adhesive surface, alternatively it may be used to denote the identity of the product or manufacturer. A chromophore that may be used as a marking agent includes methylene blue.

Typically, implantable devices according to the invention may be prepared by any convenient method of applying the coating to the device. For example, the layers of the coating may be cast on the device in an analogous manner to the way in which the materials of the structural layer or laminate and tissue-contacting layer are cast, as described above. Alternatively, the coating may be applied by dipping of a device in liquid formulations or by spraying the device with liquid formulations.

Therapeutic Applications of the Sheet

The sheet according to the invention is suitable for application to both internal and external surfaces of the body, ie it may be applied topically to the exterior of the body (eg to the skin) or to internal surfaces such as surfaces of internal organs exposed during surgical procedures, including conventional and minimally invasive surgery.

The sheet according to the invention is particularly suitable for surgical applications in the following areas:
Thoracic/cardiovascular
General surgery
ENT
Urology
Oral/maxillofacial
Orthopaedic
Neurological
Gastroenterology
Opthalmology
Gynaecology/obstetrics Possible uses are described in more detail below.

Wound Healing

The degradable nature of the sheet means that it may support and promote wound healing during both internal and topical procedures. Once the sheet begins to degrade, fibroblasts will move in and begin to deposit components of the extracellular matrix. The sheet can therefore be used as an internal or external dressing. In addition, factors such as growth factors and cAMP that are known to promote the proliferation of skin cells may be added to the formulation to assist in the healing process. The sheet may be designed to control the transmission of moisture and infectious agents, and thus be useful particularly in the treatment of burns.

Skin Closure

The sheet may be applied topically to promote wound closure (as an alternative to sutures). This may have beneficial effects in that it may reduce scarring, and the formulation and sheet may thus be useful for cosmetic purposes during minor surgery (eg in Accident & Emergency Departments). Self-adhesive properties of the sheet may make it easy to apply quickly.

Hernia Repair

The sheet may be used to provide reinforcement in hernia repair procedures. The self-adhesive attachment overcomes the potential issues faced by conventional surgical reinforcing mesh products, which require suturing or stapling in an already weakened area. The sheet for such a procedure may be engineered to have short or long term durability, depending on the degree of tissue repair required. The sheet may also be able to withstand the application of staples.

The invention may also find application in the provision of an adhesive coating to hernia mesh devices.

Anastomosis

The sheet provides a means for rapid sealing of, and prevention of leaks in, joined tubular structures such as blood vessels, and vascular and bladder grafts, and the GI tract. The ability of the sheet to support tissue repair may be of particular value if used in nerve repair.

Sealing Large Areas of Tissue

The good sealing and handling properties of the sheet, combined with its self-adhesive properties and ability to cover a large surface area, mean that it may be of particular use in sealing resected tissue surfaces—in particular those where diffuse bleeding is an issue (eg the liver). The sheet also provides an ideal support matrix for tissue repair at such sites. This could also be applicable to limiting leakage of cerebrospinal fluid following neurological surgery.

Sealing Air Leaks

In addition to the patch properties described above, the high tensile strength and good inherent elasticity of the sheet (after hydration and reaction of the tissue-reactive functional groups), make it particularly suitable for sealing air leaks in the lung, particularly following lung resection. Again, after effecting a seal, the sheet provides an ideal support matrix for tissue repair at such sites.

Haemostasis

The sheet may be applied to a bleeding area, acting as a physical barrier. The tissue-reactive material in the sheet may immobilise proteins and thereby promote haemostasis.

Therapeutic Agent Administration

Drugs, anti-infectives and other therapeutic agents (including biologically active agents such as growth factors, and even cells and cellular components) may be added to solution (s) used to form the components of the sheet, or covalently linked to components prior to their use in the manufacture of the sheet. Once the sheet is in place, following application to the desired site, the drug will be slowly released, either by diffusion or by engineering the sheet, eg by controlling the degree of cross-linking within that sheet, so that as it degrades over time the drug is released. The rate of release can be controlled by appropriate design of the sheet. The sheet may thus provide a means for delivering a known amount of drug either systemically or to a precise locus. The drug may be directly bound to a component of a solution used in the manufacture of the sheet, or simply dispersed in the solution.

Prevention of Post-Surgical Adhesions

Post-surgical adhesion, the formation of undesired connective tissue between adjacent tissues, is a serious problem which can give rise to major post-surgical complications. It is a particular problem in bowel surgery where it can cause, for instance, twisting of the bowel, which may then necessitate further surgical intervention. The application of sheet material in accordance with the invention to tissues exposed in a surgical procedure can be effective in preventing post-surgical adhesions between that tissue and neighbouring tissues.

Minimally Invasive Procedures

The use of minimally invasive techniques for taking tissue samples by biopsy, inserting devices, delivery of therapeutic agents and performing surgical procedures is rapidly developing as an alternative choice to traditional "open" surgery. Minimally invasive procedures typically result in less pain, scarring, quicker recovery time and fewer post-operative complications for patients, as well as a reduction in health care costs. Procedures are undertaken using specially designed instruments which are inserted through small keyhole-sized surgical incisions. The sheet may be introduced into the body via existing and specially designed minimally invasive surgery instruments and trocar systems, and the sheet may be shaped or prepared to an appropriate size and configuration, including buttresses for use with stapling devices. The flexibility of the sheet enables it to be formed into a configuration of reduced size, for instance by folding or rolling the sheet, and hence facilitates the use of the sheet in minimally invasive surgery procedures and/or other procedures where access is restricted. The good initial contact adhesion of the sheet to the tissue to which it is applied may also be particularly useful in such procedures.

DETAILED DESCRIPTION OF PREFERRED EMBODIMENTS

The invention will now be described in greater detail, by way of illustration only, with reference to the following Examples. Examples 1 and 2 describe the manufacture of tissue-adhesive sheets according to the invention. Examples 3 to 5 describe the performance and characteristics of such sheets. Examples 6 and 7 describe the synthesis of material containing tissue-reactive groups that is used in the sheets of Examples 1 and 2. Example 8 describes the synthesis of an alternative form of tissue-reactive material.

EXAMPLE 1

Preparation of Multi-Lamellar Sheet

Figure 1:
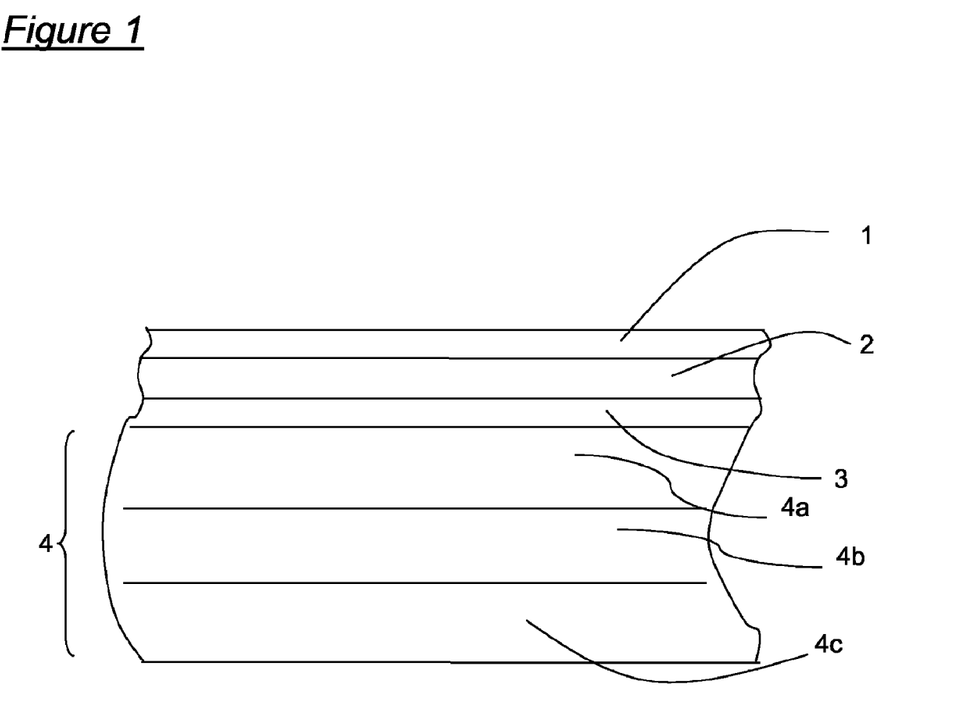
FIG. 1 shows schematically, and not to scale, the structure of an embodiment of a tissue-adhesive sheet according to the invention.

A multi-lamellar tissue-adhesive sheet according to the invention is shown schematically in FIG. 1. The sheet comprises a structural laminate and a tissue-contacting layer.

The structural laminate has the form of:
a) a first layer 1 of PLGA;
b) a second layer 2 of poly(VP-AAc-AAc(NHS)); and
c) a third layer 3 of PLGA.

The tissue-contacting layer 4 is conjoined to the third layer 3 and comprises poly(VP-AAc-AAc(NHS)).

The first and third layers 1,3 each have a thickness of approximately 4 µm, and the second layer 2 a thickness of approximately 3 µm. The tissue-contacting layer 4 has a thickness of approximately 22 µm, and consists of three sub-layers 4a-c of approximately equal thickness.

The sheet is prepared as follows:
1.1 Preparation of Solutions
    Three solutions are prepared as follows:
Solution A is 10 g PLG dissolved in 100 ml DCM.
Solution B is 7.5 g poly(VP-AAc-AAc(NHS)) dissolved in 100 ml DCM/MeOH 15/4.
Solution C is 2.5 g methylene blue dissolved in 50 ml water.
1.2 Casting of Layer 1
    Solution A is cast onto silicone backed release paper using a device referred to as a K bar. The film is dried for 30 minutes at 20° C./atmospheric pressure. The film is not removed from the release paper.
1.3 Casting of Layer 2
    Solution B is cast onto Layer 1 using a K bar. The film is dried for 30 minutes at 20° C./atmospheric pressure. The film is not removed from the release paper.
1.4 Application of Logo
    Solution C is printed onto the surface of Layer 2 to form a trade/visualisation logo.
1.5 Casting of Layer 3
    Solution A is cast onto Layer 2 using a K bar. The film is dried for 30 minutes at 20° C./atmospheric pressure. The film is not removed from the release paper.
1.6 Casting of Layer 4a to c
    Solution B is cast onto Layer 3 using a K bar. The film is dried for 30 minutes at 20° C./atmospheric pressure. The film is not removed from the release paper.
    Solution B is cast onto Layer 4a using a K bar. The film is dried for 30 minutes at 20° C./atmospheric pressure. The film is not removed from the release paper.
    Solution B is cast onto Layer 4b using a K bar. The film is dried for 16 hours at 20° C./reduced pressure. The film is not removed from the release paper.
1.7 Cutting Out
    The product is cut to size using specially designed cutters and peeled away from the release paper.
1.8 Final Drying
    The product is dried for 24 hours at 20° C./reduced pressure

EXAMPLE 2

Alternative Preparation of Multi-Lamellar Sheet

A two-layer tissue-adhesive sheet according to the invention comprises a structural layer and a tissue-contacting layer.

The structural layer has the form of a single, first layer 1 of PLGA;

The tissue-contacting layer 2 is conjoined to the first layer 1 and comprises poly(VP-AAc-AAc(NHS)).

The first layer 1 has a thickness of approximately 15 µm. The tissue-contacting layer 2 has a thickness of approximately 22 µm.

The sheet is prepared as follows:
2.1 Preparation of Solutions
    Three solutions are prepared as follows:
Solution A is 10 g PLG dissolved in 100 ml DCM.
Solution B is 10 g poly(VP-AAc-AAc(NHS)) dissolved in 100 ml DCM/MeOH 15/4.
Solution C is 2.5 g methylene blue dissolved in 50 ml water.
2.2 Casting of Layer 1
    Solution A is cast onto silicone backed release paper using a device referred to as a K bar. The film is dried for 30 minutes at 20° C./atmospheric pressure. The film is not removed from the release paper.
2.3 Casting of Layer 2
    Solution B is cast onto Layer 1 using a K bar. The film is dried for 30 minutes at 20° C./atmospheric pressure. The film is not removed from the release paper.
2.4 Application of Logo
    Solution C is printed onto the surface of Layer 2 to form a trade/visualisation logo.
2.5 Cutting Out
    The product is cut to size using specially designed cutters and peeled away from the release paper.
2.6 Final Drying
    The product is dried for 24 hours at 20° C./reduced pressure

EXAMPLE 3

In Vitro Adhesive Performance

The in vitro adhesive performance to liver of a sheet according to the invention has been quantified using a Zwick universal testing machine. After 5 minutes immersion in DPBS, the mean work of adhesion is typically 7 to 14 mJ.

EXAMPLE 4

Physical Characteristics

The product is a clear/opaque film with the logo visible throughout. Using a Zwick universal testing machine the tensile strength is quantified as typically 2 to 9 MPa.

EXAMPLE 5

In Vivo Adhesive Performance

Sheets of the type presented in Example 1 have been used to eliminate blood, fluid and air leakage from standard punch biopsy injuries to lung and liver tissue. Following application, the sheet adheres firmly to the tissue surface and results in immediate stabilisation of the injury site, resulting in satisfactory haemo- and/or pneumostasis.

Healing evaluated macroscopically and by histological examination of tissues 14 days post-application reveals good healing and sealing of the original injury site with normal tissue adjacent to the remains of the sheet. These remains are encapsulated by a thin fibrous covering. The remaining material continues to be resorbed by macrophagic activity and cellular infiltration, which is largely complete by 50 days.

EXAMPLE 6

Synthesis of poly(VP-AAc-AAc(NHS)) Terpolymer

Figure 2:
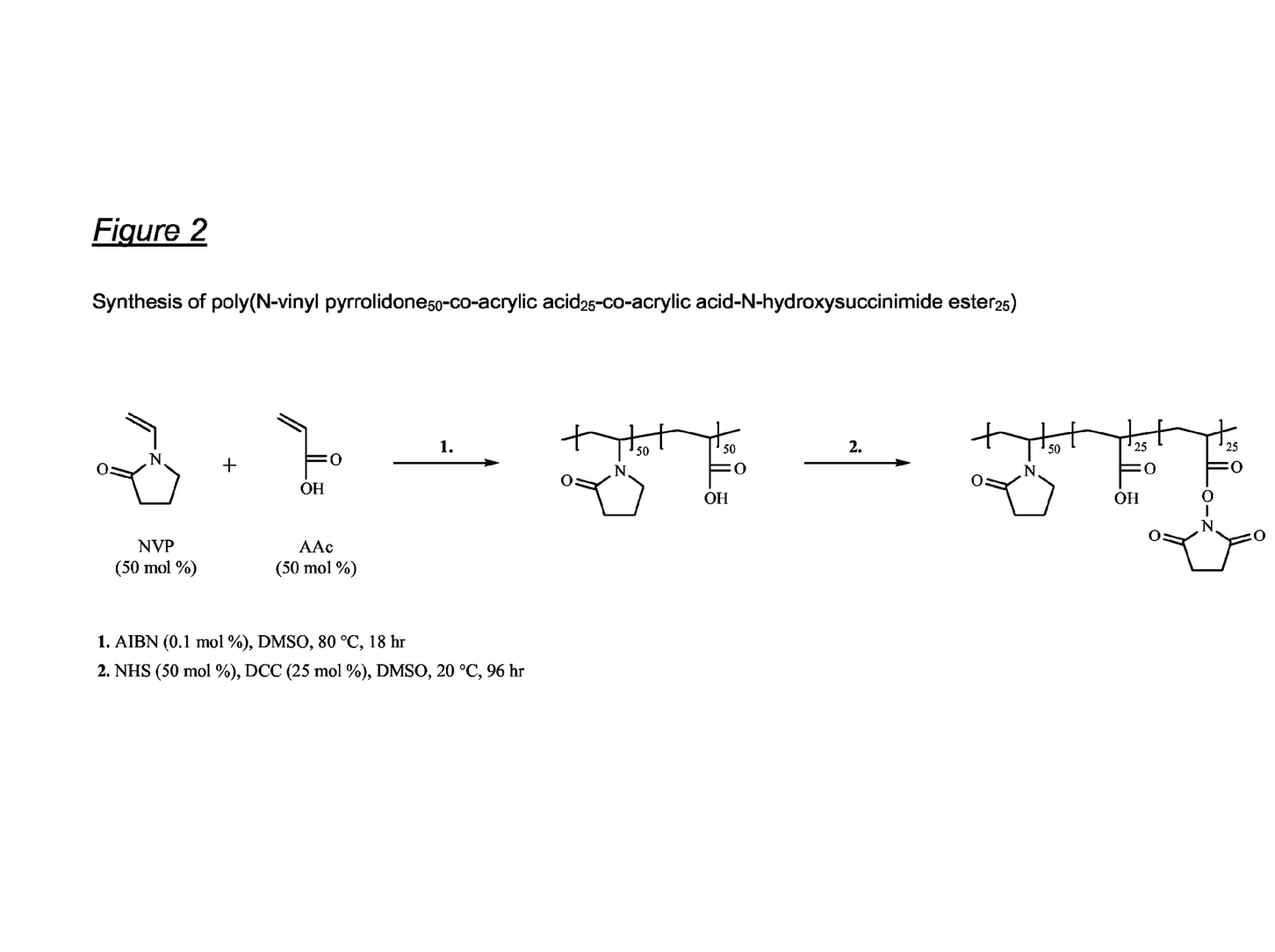
FIG. 2 illustrates the synthesis of poly(N-vinyl pyrrolidone$_{50}$-co-acrylic acid$_{25}$-co-acrylic acid-N-hydroxysuccinimide ester$_{25}$).

The reaction is shown schematically in FIG. 2.

2000 ml of deoxygenated DMSO is heated to 80° C. 121.3 g (1.09 moles) of NVP and 78.7 g (1.09 moles) of AAc are added to the DMSO followed by 0.04 g ($2.44 \times 10^{-4}$ moles) of AIBN. The reaction is left at 80° C. for 17-19 hours and then allowed to cool to room temperature. 125.6 g (1.09 moles) of NHS is dissolved in the polymer solution followed by the addition of 112.6 g (0.545 moles) of DCC dissolved in 225 ml of DMF. The reaction is left stirring at room temperature for 96 hours. The reaction by-product, DCU, is removed by filtration under reduced pressure using a sintered glass filter. The polymer is isolated by mixing with 2000 ml of IPA followed by precipitation from 13000 ml of diethyl ether followed by filtration. The polymer is washed three times in 2500 ml of diethyl ether and then dried at 40° C. under reduced pressure.

The polymer is purified further to remove trace amounts of contaminants by a Soxhlet extraction using IPA.

The Soxhlet extracted polymer is purified further by preparing a 6% w/v solution in DCM/MeOH (15/4 v/v) and then precipitation from a 50-fold excess of diethyl ether, followed by subsequent washing in diethyl ether. The purified polymer is dried at 40° C. under reduced pressure Approximate molecular weights $M_n$=2-5,000, $M_w$=10-30,000.

EXAMPLE 7

Alternative Synthesis of poly(VP-AAc-AAc(N HS)) Terpolymer 400 ml of deoxygenated toluene is heated to 80° C. 31.6 g (0.28 moles) of NVP and 20.6 g (0.28 moles) of AAc are added to the toluene immediately followed by 0.1 g ($6.1 \times 10^{-4}$ moles) of AIBN. The reaction is left at 80° C. for 17-19 hours. The polymer is isolated by precipitation in 2000 ml of 1/1 v/v hexane/diethyl ether followed by filtration under reduced pressure. The polymer is washed three times with 300 ml of diethyl ether and finally dried under vacuum at 40° C.

The acid content of the poly(VP-AAc) copolymer is determined by titration against 1.0M sodium hydroxide. 50 mol % of the acid groups are converted to NHS ester by reaction with NHS in the presence of DCC. 33.7 g of poly(VP-AAc) containing 0.77 moles of acrylic acid functionalities and 44.54 g (0.38 moles) of NHS are dissolved in 1000 ml of DMF at 25° C. 79.77 g (0.38 moles) of DCC is dissolved in 137 ml of DMF and added to the polymer solution and the reaction is stirred at 25° C. for 96 hours. The reaction by-product, DCU, is removed by filtration under reduced pressure using a sintered glass filter. The polymer is isolated by adding to 1250 ml of IPA followed by precipitation from 5000 ml of diethyl ether followed by filtration. The polymer is washed three times in 1000 ml of diethyl ether and then dried at 40° C. under reduced pressure.

The polymer may be purified further to remove trace amounts of contaminants by a number of commonly known methods, for example, Soxhlet extraction, dialysis or washing with using a suitable solvent such as IPA. Furthermore, drying at elevated temperature under reduced pressure may remove trace amounts of solvents and other volatile matter.

The polymer is purified further to remove trace amounts of contaminants by a Soxhlet extraction using IPA.

The Soxhlet extracted polymer is purified further by preparing a 6% w/v solution in DCM/MeOH (15/4 v/v) and then precipitation from a 50-fold excess of diethyl ether, followed by subsequent washing in diethyl ether. The purified polymer is dried at 40° C. under reduced pressure

EXAMPLE 8

Synthesis of HPC-Succinate NHS 10 g of HPC ($M_w$ approx 370,000) is dissolved in 350 ml of anhydrous N-methylpyrrolidone at 80° C. 1.4 g (0.014 moles) of succinic anhydride and 1.71 g (0.014 moles) of 4-dimethylaminopyridine are added. The reaction is left overnight at 80° C. The solution is cooled to room temperature and 400 ml of IPA is added. The polymer is precipitated from 3000 ml of diethyl ether, filtered and washed successively with 300 ml of diethyl ether. Finally, the polymer is dried under vacuum at 40° C.

The polymer is then dissolved in DMF and reacted with NHS in the presence of DCC to form the amine- and thiol-reactive NHS ester compound.

The invention claimed is:

1. A multi-lamellar tissue-adhesive sheet comprising a structural layer or laminate, which structural layer or laminate comprises one or more synthetic polymers having film-forming properties, and to which structural layer or laminate is conjoined a tissue-contacting layer comprising poly(VP-AAc-AAc(NHS)) terpolymer.

2. A sheet as claimed in claim 1, which comprises a structural laminate comprising two or more discrete layers that are conjoined together.

3. A sheet as claimed in claim 2, wherein the laminate comprises alternating layers of polymer having film-forming properties and material containing reactive functional groups.

4. A sheet as claimed in claim 3, which comprises a structural laminate comprising two layers of film-forming polymer with a layer of reactive material interposed therebetween, and the tissue-contacting layer.

5. A sheet as claimed in claim 4, wherein the reactive material is the same as the material of the tissue-contacting layer.

6. A sheet as claimed in claim 1, wherein the one or more polymers having film-forming properties are polyesters.

7. A sheet as claimed in claim 6, wherein the polyesters are selected from the group consisting of polylactic acid, polyglycolic acid, polycaprolactones, polyhydroxyalkanoates, and copolymers and blends of any thereof.

8. A sheet as claimed in claim 7, wherein the polyesters are selected from the group consisting of polylactic acid, polyglycolic acid, and copolymers and blends thereof.

9. A sheet as claimed in claim 8, wherein the polyester is poly(lactide-co-glycolide).

10. A sheet as claimed in claim 1, which has an overall thickness of from 0.01 to 1 mm.

11. A sheet as claimed in claim 1, which has an overall thickness of from 0.015 to 0.05 mm.

12. A sheet as claimed in claim 1, wherein the tissue-contacting layer accounts for more than 50% of the overall thickness of the sheet.

13. A sheet as claimed in claim 1, which comprises a structural laminate, which laminate comprises n layers of a film-forming polymer with n−1 layers of material containing reactive functional groups interspersed therebetween, and a tissue-contacting layer of tissue-reactive material, wherein n has a value of 1, 2 or 3.

14. A sheet as claimed in claim 13, wherein the film-forming polymer is a biodegradable polyester.

15. A sheet as claimed in claim 1, which comprises a structural laminate, which laminate comprises n layers of a biodegradable polyester with n−1 layers of material containing reactive functional groups interspersed therebetween, and a tissue-contacting layer comprising poly(VP-AAc-AAc (NHS)) terpolymer, wherein n has a value of 1, 2 or 3.

16. A sheet as claimed in claim 14, wherein the polyester is selected from the group consisting of polylactic acid, polyglycolic acid, polycaprolactones, polyhydroxyalkanoates, and copolymers and blends of any thereof.

17. A sheet as claimed in claim 16, wherein the polyester is selected from the group consisting of polylactic acid, polyglycolic acid, and copolymers and blends thereof.

18. A sheet as claimed in claim 17, wherein the polyester is poly(lactide-co-glycolide).

19. A sheet as claimed in claim 13, wherein the material containing reactive functional groups is poly(VP-AAc-AAc (NHS)).

20. A sheet as claimed in claim 13, wherein n has a value of 2.

21. A sheet as claimed in claim 20, wherein the tissue-contacting layer accounts for more than 50% of the overall thickness of the sheet.

22. A sheet as claimed in claim 21, wherein the tissue-contacting layer accounts for more than 60% of the overall thickness of the sheet.

23. A method of manufacturing a sheet as claimed in claim 1, which method comprises stepwise formation of the layer(s) of the structural layer or laminate, followed by formation of the tissue-contacting layer.

24. A method of joining a tissue surface to another tissue, or of sealing a tissue surface, which method comprises applying to the tissue surface a sheet as claimed in claim 1.

* * * * *